United States Patent
Refaai (10) Patent No.: US 10,722,608 B2
(45) Date of Patent: Jul. 28, 2020

(54) SYSTEMIC AND TOPICAL APPLICATION OF PLATELET MICROPARTICLES TO TREAT BLEEDING IN TRAUMA PATIENTS

(71) Applicant: University of Rochester, Rochester, NY (US)

(72) Inventor: Majed A. Refaai, Henrietta, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 15/554,804

(22) PCT Filed: Mar. 4, 2016

(86) PCT No.: PCT/US2016/020973
§ 371 (c)(1),
(2) Date: Aug. 31, 2017

(87) PCT Pub. No.: WO2016/141325
PCT Pub. Date: Sep. 9, 2016

(65) Prior Publication Data
US 2018/0050127 A1    Feb. 22, 2018

Related U.S. Application Data

(60) Provisional application No. 62/127,890, filed on Mar. 4, 2015.

(51) Int. Cl.
| | | |
|---|---|---|
| A61L 15/32 | (2006.01) | |
| A61L 15/40 | (2006.01) | |
| A61L 24/00 | (2006.01) | |
| A61L 24/10 | (2006.01) | |
| A61K 35/19 | (2015.01) | |
| A61K 38/36 | (2006.01) | |
| A61K 38/48 | (2006.01) | |

(52) U.S. Cl.
CPC .............. *A61L 15/32* (2013.01); *A61K 35/19* (2013.01); *A61K 38/363* (2013.01); *A61K 38/4846* (2013.01); *A61L 15/40* (2013.01); *A61L 24/0005* (2013.01); *A61L 24/108* (2013.01); *A61L 2400/04* (2013.01)

(58) Field of Classification Search
CPC .... A61K 2300/00; A61K 35/19; A61K 35/14; A61K 38/36; A61K 38/37; A61K 38/48; A61K 38/363; A61K 38/4846; A61L 15/32; A61L 15/40; A61L 2400/04; A61L 24/0005; A61L 24/108
See application file for complete search history.

(56) References Cited

U.S. PATENT DOCUMENTS

| | | |
|---|---|---|
| 5,332,578 A | 7/1994 | Chao |
| 8,105,632 B2 | 1/2012 | Jy |
| 8,349,367 B2 * | 1/2013 | Bakaltcheva ........ A61K 9/0019 424/530 |
| 2006/0034809 A1 | 2/2006 | Ho |
| 2008/0069807 A1 * | 3/2008 | Jy ......................... A61K 35/18 424/93.72 |

FOREIGN PATENT DOCUMENTS

| | | | |
|---|---|---|---|
| CN | 101072506 A | 11/2014 | |
| EP | 2403498 A2 | 1/2012 | |
| WO | 1990012581 A1 | 11/1990 | |
| WO | WO-9012581 A1 * | 11/1990 | ............ A61K 35/19 |
| WO | 2010102216 A2 | 9/2010 | |

OTHER PUBLICATIONS

Michael Merten, Circulation, 1999, pp. 2577-2582.*
P. E . J . Van Der Meijden, Platelet- and erythrocyte-derived microparticles trigger thrombin generation via factor XIIa, Journal of Thrombosis and haemostasis, 10: 1355-1362.*
Jy, W., et al. "Tu-P10: 485 Microparticles from platelets (PMP), endothelia (EMP), leukocytes (LMP), and RBC (RMP) exhibit distinct hemostatic activities: New findings on RMP." Atherosclerosis Supplements 7.3 (2006): 291-292.
Hargett, Leslie A., and Natalie N. Bauer. "On the origin of microparticles: From "platelet dust" to mediators of intercellular communication." Pulmonary circulation 3.2 (2013): 329-340.
Mallat, Ziad, et al. "Elevated levels of shed membrane microparticles with procoagulant potential in the peripheral circulating blood of patients with acute coronary syndromes." Circulation 101.8 (2000): 841-843.
Hughes, Mary, et al. "Morphological analysis of microparticle generation in heparin-induced thrombocytopenia." Blood 96.1 (2000): 188-194.
Heijnen, Harry FG, et al. "Activated Platelets Release Two Types of Membrane Vesicles: Microvesicles by Surface Shedding and Exosomes Derived From Exocytosis of Multivesicular Bodies and -Granules." Blood 94.11 (1999): 3791-3799.
Binder, Henry M., and Brian R. Smith. "In vitro evaluation of stored platelets: is there hope for predicting posttransfusion platelet survival and function?." Transfusion 43.1 (2003): 2-6.
Kaufman, Richard M. "Platelets: testing, dosing and the storage lesion—recent advances" ASH Education Program Book 2006.1 (2006): 492-496.
Murphy, Scott, and Frank H. Gardner. "Platelet preservation: effect of storage temperature on maintenance of platelet viability—deleterious effect of refrigerated storage." New England Journal of Medicine 280.20 (1969): 1094-1098.
Communication received for corresponding European Patent Application No. 16714093.8, dated Oct. 9, 2019, pp. 1-6.
Capriotti et al., 2013, "Proteomic Characterization of Human Platelet-Derived Microparticles." Analytica Chimica Acta. 776: pp. 57-63.

* cited by examiner

*Primary Examiner* — Rachael E Bredefeld
*Assistant Examiner* — Erinne R Dabkowski
(74) *Attorney, Agent, or Firm* — Riverside Law LLP (57) ABSTRACT

The present disclosure is directed to blood dotting compositions comprising platelet microparticles, method of using said compositions, and methods of preparing the same.

12 Claims, 6 Drawing Sheets

| Method Specifics | WO 1990/012581 to Chao | 2006/0034809 to Ho | 8,105,632 to Jy Stored Blood Method | 8,105,632 to Jy Ultrasonic Method | 8,105,632 to Jy Calcium Activation Method | Composition of Present Disclosure |
|---|---|---|---|---|---|---|
| Platelet (Plt) | expired BB plt bag | Fresh PRP pH 6.6-6.8 adjusted with ACD | 1-5 day expired BB plt bag | Fresh | 1mL washed plts | Fresh |
| PRP centrifuge | 11x100 rpm/ 11 min @22C. 30x100rpm/ 25min @22C | 500xg for 5 min | n/a | n/a | n/a | 130xg for 12 min |
| wash step | 2x NS 30x100 rpm/ 20 min. | plt pelleted at 1500xg for 15 min. | n/a | 2x PBS with 1mM EDTA/5mM MgSO4 | n/a | None for topical applications; For systemic application product: PLT washed with MPBS, centrifuged at 2200xg for 10 min x2 |
| plt concentration | n/a | resuspended in 5% original volume in Tyrodes with trehalose. 1250x10³ | plt sedimented at 200xg for 10 min | 250x10³ | 250x10³ in HEPES/saline pH 7.4 | Spun at 370xg for 8 min. Discard the top 75% of PPP. PLT is re-suspended in the remaining 25% of PPP to concentrate to ($\geq 10^6$) |
| supernatant treatment | n/a | n/a | supernatant diluted 1:1 with PBS/citrate solution. | n/a | n/a | n/a |

Figure 2B

| Method Specifics | WO 1990/012581 to Chao | 2006/0034809 to Ho | 8,105,632 to Jy Stored Blood Method | 8,105,632 to Jy Ultrasonic Method | 8,105,632 to Jy Calcium Activation Method | Composition of Present Disclosure |
|---|---|---|---|---|---|---|
| freeze/thaw | 3x frozen -80C for >6 hrs/thaw >1hr at RT. | n/a | n/a | n/a | n/a | frozen @ -20°C for at least 24 hrs, thawed at 37°C water bath for 5 min |
| wash step | 3x NS 30x100rpm/20min | n/a | n/a | n/a | n/a | n/a |
| heat treatment | 100C for 5 min | 37C for 2 hrs mixing every 30 min | n/a | n/a | n/a | n/a |
| sonication | pulsing 20hz (1.4s on/0.6s off) for 5min 48sec | n/a | n/a | 3-5 bursts for 3-5 seconds | n/a | 2 sec on/off x 4 times. (8 sec total) |
| ice during sonication | no | no | n/a | no | no | yes |
| plt activation | n/a | n/a | n/a | n/a | thrombin + collagen agitated at RT for 20 min | n/a |
| MP isolation | Spin sonicated solution at 30x100 rpm for 30 minutes. Supernatant collected and stored at 4C | n/a | 8,000xg for 30 mins to sediment MP. Resuspend in PBS/citrate. Place in fridge until testing. Wash/resuspend in saline prior to use. | spin at 200xg for 10 min. Spin supernatant 8,000xg for 30 min. wash/resuspend with desired iv solution | spin at 200xg for 10 min. Spin supernatant 8,000xg for 30 min. wash/resuspend with desired iv solution | Spun at 18,000xg for 60 min at RT. Discard the top 75% of PPP, Concentrated PMP is re-suspended in the remaining 25% PPP |
| Diluent | n/a | n/a | n/a | n/a | n/a | MPBS for systemic application, none for topical application |

Figure 2C

| Method Specifics | Normal Range | WO 1990/012581 to Chao | 2006/0034809 to Ho | 8,105,632 to Jy Stored Blood Method | 8,105,632 to Jy Ultrasonic Method | 8,105,632 to Jy Calcium Activation Method | Composition of Present Disclosure Topical | Composition of Present Disclosure Systemic |
|---|---|---|---|---|---|---|---|---|
| R time | 5 – 10 min | 7.8 | 2.1 | 3.9 | 4.2 | 2.7 | 1.2 | 2.1 |
| K time | 1 – 3 min | 5.2 | 3.1 | 5.2 | 10.6 | 8.9 | 2.2 | 1.9 |
| α angle | 53 - 72 ° | 43.7 | 56.3 | 48.3 | 35.3 | 41.3 | 74 | 75 |
| Maximum Amplitude | 50 – 70 mm | 38.4 | 47.5 | 32.5 | 25.6 | 30.9 | 48 | 49 |
| CI | -3 - 3 | -6.8 | -0.2 | -4.7 | -8.7 | -6 | 0.7 | 1.8 |
| Coag Tests | | | | | | | | |
| PT | 9 – 14 sec | failed >100 | failed >100 | failed >100 | failed >100 | failed >100 | 11 | 17 |
| PTT | 25 – 50 sec | failed >200 | failed >200 | failed>200 | failed>200 | failed >200 | 44 | 51 |
| PLT count | 150 – 350 x$10^3$/microL | 0 | 659 x $10^3$ | 5 x $10^3$ | 0 | 26 x $10^3$ | 1.2 x $10^6$ | 0.8 x $10^6$ |
| WBC count | 0.5 – 10 x$10^3$/microL | 0 | 0.02 | 0 | 0 | 0 | 0 | 0 |
| Fibrinogen | 172 – 409 mg/dL | failed -0 | failed -0 | failed - 0 | failed<30 | failed - 0 | 334 | 350 |
| vW activity | 37 - 174 % | failed - 0 | failed - 0 | failed - 0 | failed - 0 | failed - 0 | 26 | 24.2 |
| vW antigen | 44 – 166 % | failed - 0 | failed - 0 | failed - 0 | 0 | 4 | 146 | 51.7 |
| Factor V (IU) | 0.67 – 1.39 | 0.001 | 0.001 | 0 | 0 | 0 | 0.81 | 0.89 |
| Factor VII (IU) | 0.66 – 1.59 | 0.002 | 0.002 | 0.009 | 0.001 | 0.004 | 1.06 | 1.92 |
| Factor VIII (IU) | 0.68 – 1.59 | 0 | 0.006 | 0 | 0 | 0.001 | 0.78 | 0.76 |
| Factor XI (IU) | 0.69 – 1.54 | 0 | 0 | 0 | 0 | 0 | 1.02 | 1.09 |
| Factor IX (IU) | 0.92 – 1.61 | 0 | 0 | 0 | 0 | 0 | 0.82 | 1.01 |

Figure 3    Control plasmas run on Calibrated Automated Thrombogram (CAT)

Figure 4

TGA

(Stago, Calibrated Automated Thrombogram®)

| Sample | Lag time | Time to Peak | Peak | ETP | Velocity Index |
|---|---|---|---|---|---|
| Units | Min | min | nmol/L | nmol/L/min | nmol/L/min |
| Fresh PRP | 4.44 ± 0.16 | 11.1 ± 0.4 | 145.3 ± 3.8 | 1330.1 ± 17.2 | 21.9 ± 1.4 |
| Stored PRP | 5.89 ± 0.16 | 10.1 ± 0.16 | 89.4 ± 8.8 | 876.3 ± 67.9 | 21.4 ± 3.5 |
| PMP | 5.22 ± 0.16 | 10.67 ± 0 | 173.7 ± 2.2* | 1437.6 ± 11.5* | 31.9 ± 0.86* |

\* P value < 0.001 in comparison to stored and fresh platelets

SYSTEMIC AND TOPICAL APPLICATION OF PLATELET MICROPARTICLES TO TREAT BLEEDING IN TRAUMA PATIENTS

CROSS-REFERENCE TO RELATED APPLICATIONS

This application claims priority to U.S. Provisional Application Ser. No. 62/127,890, filed Mar. 4, 2015, the content of which is incorporated by reference herein in its entirety.

BACKGROUND OF THE INVENTION

Platelets are anuclear cell fragments shed from bone marrow megakaryocytes that circulate through the vascular system. Platelets play two major roles in hemostasis: adhesion to the walls of damaged blood vessels, leading to the formation of a platelet plug; and activation of platelet-dependent blood coagulation pathways, essential for the formation of a fibrin clot. Thus platelets are critical for blood clot initiation and the control of patient bleeding (i.e., hemorrhaging) due to injury, trauma, bleeding disorders, or medical interventions.

Blood clot initiation begins with the adhesion of platelets to the wall of an injured vessel. von Willebrand factor ("vWF") bind to platelets and help them attach to collagen present in the surrounding tissues at the site of injury forming the initial platelet clot. Fibrinogen, a soluble plasma protein, is converted to insoluble strands of fibrin by the enzyme thrombin (which is activated by activated Factor X). Thrombin also converts Factor XIII to activated Factor XIIIa. Fibrin filaments are then cross-linked by Factor XIIIa to form a fibrin-platelet mesh referred to as a fibrin clot.

Coagulation factor X can be activated by two distinct pathways, termed the extrinsic and intrinsic pathways. The extrinsic pathway is activated by sub-endothelial tissue factor ("TF"), which is not normally present in the lumen of intact blood vessels. Blood vessel disruption exposes circulating clotting factors to TF. Factor VII is activated to Factor VIIa, which in turn activates Factor X to Factor Xa. In contrast, activation of the intrinsic pathway does not always require TF, especially in vitro. The intrinsic pathway is activated by contact with negatively charged substances, such as contact with sub-endothelial collagen in vivo, or glass in vitro—Factor XII is activated to Factor XIIa, which converts Factor XI to Factor XIa. In the presence of calcium ions, Factor XIa activates Factor IX to IXa, which in turn combines with Factor VIII to activate circulating Factor X. Thus, the activation of blood clotting is dependent on a cascade of several coagulation factors in conjunction with the activity of platelets. In addition, one or more coagulation factor tests may be performed to evaluate the concentration and/or activity of specific coagulation factors (i.e., fibrinogen, vWF, Factor V, Factor VII, Factor VIII, Factor IX, Factor XI, and Factor XII).

As such, patient hemostasis is often evaluated by analyzing a patient blood sample for platelet counts, various markers involved in blood clotting, and clot forming ability, including the amount of time it takes to clot initiation. The coagulation assays measuring the prothrombin time ("PT") and the partial thromboplastin time ("PTT") or otherwise known as activated partial thromboplastin time ("aPTT") are used to evaluate the extrinsic and intrinsic coagulation pathways, respectively. Thromboelastography ("TEG") is another method of testing the efficiency of blood coagulation. It is mainly used in surgery and anesthesiology and has been established as a sensitive test for hemostatic function in several clinical settings. TEG measures coagulation factor activity, platelet function, clot strength, and fibrinolysis by triggering clot formation followed by computerized coagulation analysis. These assays allow the detection of blood clotting diseases, disorders, or complications arising from diseases, treatments, injuries, surgical procedures, and/or trauma.

While excessive clotting can cause blood vessel occlusion, insufficient or weak clotting can result in excessive blood loss. Treatment of platelet deficiency (a condition referred to as thrombocytopenia) involves the transfusion of stored, concentrated, platelets prepared from donated blood units. Refrigeration of platelets prior to transfusion inhibits platelet function and results in rapid clearance from the circulation (Murphy et al., "Effect of Storage Temperature on Maintenance of Platelet Viability—Deleterious Effect of Refrigerated Storage," N Engl. J. Med. 280:1094-1098 (1969)). Thus, platelets are best stored at room temperature. Because room temperature storage has the downside of promoting bacterial growth, platelet storage is ordinarily limited to a maximum of 5 days, making platelet inventory management extremely challenging (Kaufman R M, "Platelets: Testing, Dosing, and the Storage Lesion—Recent Advances," Hematology Am. Soc. Hematol. Educ. Program. 1:492-6 (2006)).

Stored platelets survive and function after transfusion with varying degrees of success. Platelets that have been gently prepared and then immediately transfused without a significant storage interval (within 24-48 hours of donation) have uniformly high recovery, good survival, and preserved function. However, practically this is not possible since blood products have to be cleared from any infectious diseases before transfusion; a process that take up to 48 hours. Thus, the earliest platelet transfusion is at least 48 hours old. By contrast, after storage for 7 days, occasional platelet units will actually become nonviable, such that these platelets demonstrate virtually no survival following transfusion (Rinder et al., "In Vitro Evaluation of Stored Platelets: Is There Hope for Predicting Posttransfusion Platelet Survival and Function?," Transfusion. 43:2-6 (2003)).

Nonviability is most often seen following severe pH and metabolic derangement. During storage, platelets continue to be metabolically active. Products of metabolism such as lactate accumulate, and the pH falls. It has been shown that if the pH drops below 6.0-6.2, survival in vivo is severely diminished. Platelet aggregation responses to a number of agonists also significantly drop during storage (Kaufman R M, "Platelets: Testing, Dosing, and the Storage Lesion—Recent Advances," Hematology Am. Soc. Hematol. Educ. Program. 1:492-6 (2006)). No in vitro assay has yet been validated to reliably predict platelet survival in vitro (Kaufman R M, "Platelets: Testing, Dosing, and the Storage Lesion—Recent Advances," Hematology Am. Soc. Hematol. Educ. Program. 1:492-6 (2006)).

Platelets, like other cell types, shed small 0.1-1 micron fragments of their plasma membrane (referred to as microparticles). In particular, platelet microparticles ("PMPs") account for approximately 70-90% of the total microparticles ("MPs") in circulation. The average concentration of PMP in circulation in a healthy individual is approximately $2 \times 10^4$ PMP/µl. During storage, the number of PMPs present in a platelet preparation increases with time, such that large quantities of PMPs are transfused together with platelets (Heijnen et al., "Activated Platelets Release Two Types of Membrane Vesicles: Microvesicles by Surface Shedding and Exosomes Derived from Exocytosis of Multivesicular Bodies and Alpha Granules," Blood. 94:3791-94

(2000)). In vivo, PMPs have been observed in clinical situations associated with platelet activation and procoagulant activity (i.e., heparin-induced thrombocytopenia, arterial thrombosis, idiopathic thrombocytopenic purpura, thrombic thrombocytopenia, and sickle cell disease) (Hughes et al., "Morphological Analysis of Microparticle Generation in Heparin-Induced Thrombocytopenia," *Blood.* 96:188-94 (2000) and Mallat et al., "Elevated Levels of Shed Membrane Microparticles with Procoagulant Potential in the Peripheral Circulating Blood of Patients with Acute Coronary Syndromes," *Circulation.* 101:841-3 (2000)), suggesting roles for PMPs in coagulation, cellular signaling, vascular injury, and homeostasis (Hargett et al., "On the Origin of Microparticles: From 'Platelet Dust' to Mediators of Intercellular Communication," *Pulm. Circ.* 3:329-40 (2013)).

Methods for the isolation of platelet microparticles have been previously described in the literature. For example, international patent publication WO 1990/012581 to Chao discloses a method for the generation of PMPs from stored blood. U.S. Pat. App. Publ. 2006/0034809 to Ho et al. discloses compositions comprising freeze-dried platelets and freeze-dried platelet microparticles. Furthermore, U.S. Pat. No. 8,105,632 to Jy et al. discloses three alternative methods for PMP production. The methods include acidification of stored platelet concentrates, the sonication of freshly isolated or stored platelets, and treatment of platelets with calcium ionophore in the presence of calcium to induce platelet activation and PMP production.

Although numerous groups have developed methods for making isolated platelet microparticle compositions, there exists a need for improved PMP compositions that can restore normal hemostasis in bleeding patients, that are freshly prepared, suitable for long-term storage (up to 12 months), and that remain efficacious for periods extending beyond 5 days from preparation.
The disclosure herein is directed to overcoming these and other deficiencies in the art.

SUMMARY OF THE INVENTION

A first aspect is directed to a blood clotting composition that comprises isolated platelet microparticles; one or more coagulation factors selected from fibrinogen, von Willebrand factor, Factor V, Factor VII, Factor VIII, Factor IX, Factor XI, and Factor XII; and a pharmaceutical carrier.

A second aspect is directed to a blood clotting composition that comprises isolated platelet microparticles at a concentration effective to achieve a blood clot initiation time of less than two minutes when measured using thromboelastography; and a pharmaceutical carrier.

Other aspects are directed to wound dressings that comprise one or more of the blood clotting composition(s) of the present invention and a wound dressing material.

A third aspect is directed to a method of preparing a composition of platelet microparticles having coagulation activity. This method involves obtaining a sample of fresh platelet rich plasma; subjecting said sample to one or more freeze-thaw cycles; sonicating the subjected sample to induce platelet microparticle production in the sample; separating a platelet microparticle fraction from other components in the sonicated sample; and resuspending the separated platelet microparticles in an isotonic solution.

Several blood clotting compositions comprising platelet microparticles have been described in the literature. However, none of these compositions as prepared are as effective at restoring normal hemostasis, are suitable for long-term storage (up to 12 months), and remain efficacious for periods extending beyond 5 days from preparation as the preparations described herein.

In one embodiment, the composition of the invention can be stored at −20° C. for 1 year and maintain therapeutic properties. In one embodiment, the composition of the invention can be stored at −80° C. for 7 years and maintain therapeutic properties.

In one embodiment, the composition of the invention can be diluted as needed for the appropriate type of applications. A stabilizer can be added to the composition of the invention.

In one embodiment, the composition of the invention can be pathogen inactivated.

In one embodiment, the composition of the invention can be in a liquid format including but not limited to wet bandage, spray (e.g, for skin injuries or bleeding sites), syringe, IV solution, and the likes.

In one embodiment, the composition of the invention can be in any desired form including but not limited to powder, gel, foam, and the likes.

In one embodiment, the composition of the invention can be used in any therapeutic situations including but is not limited to topical application on injured/trauma surfaces, IV infusion in bleeding patients, topical application on bleeding sites by anesthesia/surgeons.

BRIEF DESCRIPTION OF THE DRAWINGS

FIGS. 1A-1F are thromboelastography ("TEG") graphs of platelet blood samples.

FIG. 3 shows that thrombin, which is activated Factor II, is better/stronger formed using the composition of the invention in comparison to fresh donor PRP.

DETAILED DESCRIPTION OF THE INVENTION

The disclosure herein relates generally to blood clotting compositions comprising platelet microparticles ("PMPs"), methods of using such compositions, and methods of preparing such compositions.

In one embodiment, the composition of the invention can be generated form an O donor to be universal.

In one embodiment, the composition of the invention can be pathogen reduced or pathogen inactivated.

In one embodiment, the composition of the invention can be washed and administrated intravenously.

In one embodiment, the composition of the invention can be stored for long periods of time without specific requirements and yet maintain biological activity.

In one embodiment, the composition of the invention improves and expedites the clotting process.

In one embodiment, the composition of the invention is a concentrated product.

In one embodiment, the composition comprises PMP at a concentration of about $1.0 \times 10^4$-$1.0 \times 10^{12}$ particles/mL. In one embodiment, the composition comprises PMP at a concentration of about $1.0 \times 10^5$-$1.0 \times 10^{11}$ particles/mL. In one embodiment, the composition comprises PMP at a concentration of about $1.0 \times 10^6$-$1.0 \times 10^{10}$ particles/mL. In one embodiment, the composition comprises PMP at a concentration of about $1.0 \times 10^7$-$1.0 \times 10^9$ particles/mL. In one embodiment, the composition comprises PMP at a concentration of about $3.9 \times 10^8$-$5.5 \times 10^8$ particles/mL, as measured by NanoSight. In one embodiment, the composition comprises PMP at a concentration of about $4.0 \times 10^7$-$5.0 \times 10^7$ particles/mL, as measured by flow cytometry.

In one embodiment, the size of each PMP is about 10-1000 nm. In one embodiment, the size of each PMP is about 50-750 nm. In one embodiment, the size of each PMP is about 75-500 nm. In one embodiment, the size of each PMP is about 100-400 nm. In one embodiment, the size of each PMP is about 200-300 nm. In one embodiment, the size of each PMP is about 260-290 nm. In one embodiment, the size of each PMP is about 276 nm.

In one embodiment, the pH of the composition is about 7.0-10.0. In one embodiment, the pH of the composition is about 7.5-9.0. In one embodiment, the pH of the composition is about 8.0-8.5 In one embodiment, the pH of the composition is about 8.1-8.4. In one embodiment, the pH of the composition is about 8.2.

In one embodiment, the composition comprises a platelet (PLT) count of about $1.0 \times 10^3$-$1.0 \times 10^{10}$ $\mu L^{-1}$. In one embodiment, the composition comprises a PLT count of about $1.0 \times 10^4$-$1.0 \times 10^9$ $\mu L^{-1}$. In one embodiment, the composition comprises a PLT count of about $1.0 \times 10^5$-$1.0 \times 10^8$ $\mu L^{-1}$. In one embodiment, the composition comprises a PLT count of about $1.0 \times 10^6$-$1.0 \times 10^7$ $\mu L^{-1}$.

In one embodiment, the composition comprises a white blood cell count (WBC) of about $0$-$1.0 \times 10^5$ $\mu L^{-1}$. In one embodiment, the composition comprises a WBC of about $0$-$1.0 \times 10^4$ $\mu L^{-1}$. In one embodiment, the composition comprises a WBC of about $0$-$1.0 \times 10^3$ $\mu L^{-1}$. In one embodiment, the composition comprises a WBC count of about $0$-$0.2 \times 10^3$ $\mu L^{-1}$.

In one embodiment, the composition comprises fibrinogen (Fib or Factor I) at a concentration of about 10-1000 mg/deciliter (dL). In one embodiment, the composition comprises Fib at a concentration of about 50-500 mg/dL. In one embodiment, the composition comprises Fib at a concentration of about 100-400 mg/dL. In one embodiment, the composition comprises Fib at a concentration of about 150-375 mg/dL. In one embodiment, the composition comprises Fib at a concentration of about 180-368 mg/dL.

In one embodiment, Factor V (FV) is present in the composition at about 0.5-2.0 International Unit (IU). In one embodiment, FV is present in the composition at about 0.6-1.5 IU. In one embodiment, FV is present in the composition at about 0.7-1.25 IU. In one embodiment, FV is present in the composition at about 0.81-0.94 IU. The normal range of FV is about 0.67-1.39 IU.

In one embodiment, Factor VII (FVII) is present in the composition at about 0.5-4.0 IU. In one embodiment, FVII is present in the composition at about 0.75-3.0 IU. In one embodiment, FVII is present in the composition at about 1.0-2.5 IU. In one embodiment, FVII is present in the composition at about 1.5-2.25 IU. In one embodiment, FVII is present in the composition at about 1.57-2.08 IU. The normal range of FVII is about 0.66-1.59 IU.

In one embodiment, Factor VIII (FVIII) is present in the composition at about 0.2-2.0 IU. In one embodiment, FVIII is present in the composition at about 0.3-1.0 IU. In one embodiment, FVIII is present in the composition at about 0.4-0.9 IU. In one embodiment, FVIII is present in the composition at about 0.5-0.85 IU. In one embodiment, FVIII is present in the composition at about 0.6-0.8 IU. In one embodiment, FVIII is present in the composition at about 0.65-0.78 IU. The normal range of FVIII is about 0.68-1.56 IU.

In one embodiment, Factor IX (FIX) is present in the composition at about 0.5-3.0 IU. In one embodiment, FIX is present in the composition at about 0.6-2.0 IU. In one embodiment, FIX is present in the composition at about 0.7-1.75 IU. In one embodiment, FIX is present in the composition at about 0.8-1.5 IU. In one embodiment, FIX is present in the composition at about 0.82-1.45 IU. The normal range of FIX is about 0.92-1.61 IU.

In one embodiment, Factor XI (FXI) is present in the composition at about 0.5-3.0 IU. In one embodiment, FXI is present in the composition at about 0.7-2.0 IU. In one embodiment, FXI is present in the composition at about 0.9-1.75 IU. In one embodiment, FXI is present in the composition at about 1.0-1.5 IU. In one embodiment, FXI is present in the composition at about 1.02-1.49 IU. The normal range of FXI is about 0.69-1.54 IU.

In one embodiment, Factor XII (FXII) is present in the composition at about 1.0-7.0 IU. In one embodiment, FXII is present in the composition at about 1.25-6.0 IU. In one embodiment, FXII is present in the composition at about 1.5-5.5 IU. In one embodiment, FXII is present in the composition at about 1.75-5.0 IU. In one embodiment, FXII is present in the composition at about 1.95-4.53 IU. The normal range of FXII is about 0.57-1.63 IU.

In one embodiment, percent activity of von Willebrand (vW): Ag in the composition is about 100-300%. In one embodiment, percent activity of vW: Ag in the composition is about 120-250%. In one embodiment, percent activity of vW: Ag in the composition is about 140-200%. In one embodiment, percent activity of vW: Ag in the composition is about 146-191%. The normal range of percent activity of vW: Ag is about 44-166% activity.

In one embodiment, percent activity of vW: Act in the composition is about 10-100%. In one embodiment, percent activity of vW: Act in the composition is about 15-80%. In one embodiment, percent activity of vW: Act in the composition is about 20-60%. In one embodiment, percent activity of vW: Ag in the composition is about 23-40%. The normal range of percent activity of vW: Ag is about 37-174% activity.

In one embodiment, percent activity of protein C (PC) in the composition is about 25-300%. In one embodiment, percent activity of PC in the composition is about 50-250%. In one embodiment, percent activity of PC in the composition is about 75-200%. In one embodiment, percent activity of PC in the composition is about 100-150%. In one embodiment, percent activity of PC in the composition is about 105-142%. The normal range of percent activity of PC is about 37-174% activity.

In one embodiment, percent activity of protein S (PS) in the composition is about 10-150%. In one embodiment, percent activity of PS in the composition is about 20-100%. In one embodiment, percent activity of PS in the composition is about 30-80%. In one embodiment, percent activity of PS in the composition is about 40-70%. In one embodiment, percent activity of PS in the composition is about 50-65%. In one embodiment, percent activity of PS in the composition is about 54-62%. The normal range of percent activity of PS is about 37-174% activity.

In one embodiment, percent activity of antithrombin III (ATIII) in the composition is about 25-250%. In one embodiment, percent activity of ATIII in the composition is about 50-200%. In one embodiment, percent activity of ATIII in the composition is about 70-150%. In one embodiment, percent activity of ATIII in the composition is about 80-125%. In one embodiment, percent activity of ATIII in the composition is about 85-105%. The normal range of percent activity of ATIII is about 37-174% activity.

In one embodiment, the composition comprises Hgb at a concentration of about 0-1 mg/dL. In one embodiment, the composition comprises Hgb at a concentration of about 0-0.5 mg/dL. In one embodiment, the composition comprises Hgb at a concentration of about 0 mg/dL.

In one embodiment, the composition comprises a hematocrit (Hct) of about 0-1%. In one embodiment, the composition comprises an Hct of about 0-0.5%. In one embodiment, the composition comprises an Hct of about 0%.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2012, Current Protocols in Molecular Biology, John Wiley & Sons, NY), which are provided throughout this document.

The nomenclature used herein and the laboratory procedures used in analytical chemistry and organic syntheses described elsewhere herein are those well-known and commonly employed in the art. Standard techniques or modifications thereof are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, or ±10%, or ±5%, or ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

By "coagulation factor" is meant a polypeptide, analog, or fragment thereof having at least 85, 90, 95, 96, 97, 98, 99 or 100% amino acid sequence identity to a member of the proteins involved in the coagulation cascade, by which blood clots are formed. Exemplary coagulation factors include Factor VIII, Factor IX, Factor XI, and Factor XII. Disorders of coagulation include hemophilia, which is due to a deficiency of Factor VIII or Factor IX.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

By "platelet" is meant a non-nucleated disk-shaped cell formed in the megakaryocyte and found in the blood of all mammals. Platelets are frequently involved in blood coagulation.

"Sample" or "biological sample" as used herein means a biological material from a subject, including but is not limited to organ, tissue, exosome, blood, plasma, saliva, urine and other body fluid. A sample can be any source of material obtained from a subject.

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Accordingly, a first aspect relates to a blood clotting composition that comprises isolated platelet microparticles; one or more coagulation factors selected from fibrinogen (Factor I), von Willebrand factor, Factor II, Factor V, Factor VII, Factor VIII, Factor IX, Factor X, Factor XI, and Factor XII; and a pharmaceutical carrier.

In one embodiment, the blood clotting composition comprises components set forth in Table 3.

Another aspect relates to a blood clotting composition that comprises isolated platelet microparticles at a concentration effective to achieve a blood clot initiation time of less than two minutes when measured using thromboelastography, and a pharmaceutically acceptable carrier.

Platelet microparticles ("PMP") are ~0.1-1 micrometer microparticles released from platelets in association with platelet activation, stress, or apoptosis, the contents of which include platelet granular proteins such as P-selectin, and various platelet surface membrane glycoproteins such as glycoprotein (GP)IbAX or GPIIb/IIIa.

The isolated platelet microparticles of the present composition can be obtained from any source, including, but not limited to, mammals, such as humans, dogs or other canines, cats or other felines, mice, rats, or other rodents; pigs, horses, sheep, goats, cows, or other farm animals; and monkeys, chimps, apes, or other primates. That is, the compositions can comprise platelet microparticles from any mammalian species, including, but not limited to, humans, primates, canines, felines, bovines, ovines, porcines, equines, and rodents. In addition, the platelet microparticles can be autologous or heterologous, with respect to the other blood components of the composition with which they are mixed in the methods disclosed herein. The platelet microparticles may be, but are not necessarily, obtained from the same patient as the other blood components of the composition (i.e., autologous platelets). However, in some embodiments, the platelets are obtained from one or more individuals other than the patient (i.e., heterologous platelets). In certain embodiments platelet microparticles originate from a pool of platelet microparticles obtained from two or more donors.

The concentration of platelet microparticles in the composition described herein may be $>10^{12}$ microparticles/$\mu$l, $>5\times10^{12}$ microparticles/$\mu$l, $>10^{13}$ microparticles/$\mu$l, or $>5\times10^{13}$ microparticles/$\mu$l. In one embodiment, the concentration of platelet microparticles in the blood clotting compositions described herein is >$10^{14}$ microparticles/μl. For example, the concentration of microparticles in the composition may be between 1-9×$10^{14}$ microparticles/μl, between 2-8×$10^{14}$ microparticles/μl, between 3-7×$10^{14}$ microparticles/μl, or between 4-6×$10^{14}$ microparticles/μl.

The platelet microparticles of the compositions described herein may be subjected to various treatments prior to use in treating a subject. In general, platelet microparticles are obtained from platelet rich plasma or from whole blood. They can be concentrated by any suitable method, including, but not limited to, centrifugation and filtration as described herein. In addition to concentration, they can be washed one or more times with saline or another suitable solution to remove some or all other blood components. Likewise, they can be maintained as a packed concentrate, having little or essentially no liquid medium surrounding them, or suspended in a suitable aqueous solution or buffer that may contain stabilizers or other substances that are compatible with platelet microparticles. They can also be filtered or prepared from a filtered product and can be pathogen treated to inactivate a broad spectrum of viruses and bacteria; a process intended to reduce the risk of transfusion transmitted infections that is very essential in the systemic used applications. Topical antibiotics can also be added to the topical used applications to minimize risk of contaminations.

The blood clotting compositions described herein may contain at least one or more coagulation factors. Suitable coagulation factors include any molecule, or analog thereof, naturally occurring or recombinantly produced, which prevents or decreases the duration of a bleeding episode in a subject. Exemplary coagulation factors include, but are not limited to, fibrinogen, von Willebrand factor, Factor V, Factor VII, Factor VIII, Factor IX, Factor X, Factor XI, Factor XII, kininogen, prekallikrein, kallikrein, tissue factor, thrombin, and prothrombin. In one embodiment, the blood clotting composition comprises at least two, at least three, at least four, at least five, or at least six coagulation factors selected from fibrinogen, von Willebrand factor, Factor V, Factor VII, Factor VIII, and Factor XI. Additionally, the composition may further comprise one or more co-factors important for coagulation factor function. For example, the composition may comprise calcium, phospholipid, and vitamin K.

The one or more coagulation factors of the blood clotting compositions may be human coagulation factors or non-human coagulation factors, e.g., derived from a non-human primate or any mammal. The one or more coagulation factors can also be chimeric coagulation factors, e.g., the coagulation factors can comprise a portion of a human coagulation factor and a portion of any non-human coagulation factor or a portion of a first non-human coagulation factor and a portion of a second non-human coagulation factor.

The one or more coagulation factors of the blood clotting composition described herein may be activated coagulation factors. Alternatively, the one or more coagulation factors can be in an inactive form, e.g., zymogens. Inactive coagulation factors can be activated subsequent to administration to a subject. Alternatively, inactive coagulation factors can be activated prior to administration.

The coagulation factors of the blood clotting composition are present at a concentration or at an activity level in the blood clotting composition that is effective for the promotion of coagulation. For example, the concentration of fibrinogen in the composition is within the normal reference range of 172-409 mg/dL, which is indicative of normal clotting activity. Likewise, von Willebrand (vW) factor and other coagulation factors are present in the composition at a concentration or activity level corresponding to a level effective for blot clot formation, e.g., the reference range of vW antigen activity is 44-166% activity of normal (where 100% is normal), the reference range of vW factor ristocetin cofactor activity is 37-174% of normal activity, the reference range of Factor V coagulant activity is 67-139% of normal activity, the reference range of Factor VII coagulant activity is 66-159% of normal activity, the reference range of Factor VIII coagulant activity is 68-159% of normal activity, and the reference range of Factor XI activity is 69-154% of normal activity. Laboratory tests to measure the coagulant activity levels of the various factors or their concentration are well known and routinely practiced in the art.

The pharmaceutically acceptable carrier component of the blood clotting composition described herein comprises any acceptable material, composition or vehicle, such as a liquid or solid filler, diluent, excipient, solvent or an encapsulating material such as liposomes, polyethylene glycol (PEG), PEGylated liposomes, nanoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Exemplary pharmaceutical carriers are described in, e.g., "Remington's Pharmaceutical Sciences" and "Encyclopedia of Pharmaceutical Technology", J. Swarbrick, and J. C. Boylan (Eds.), Marcel Dekker, Inc: New York (1988). Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, ethyl cellulose and cellulose acetate; (iv) powdered tragacanth; (v) malt; (vi) gelatin; (vii) talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol; (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline; (xviii) Ringer's solution; (xix) ethyl alcohol; (xx) phosphate buffer solutions; and (xxi) other non-toxic compatible substances employed in pharmaceutical formulations. The optimal pharmaceutically acceptable carrier may vary depending upon the route of administration and desired dosage. Pharmaceutically acceptable carriers will preferably produce liquid or semi-liquid (e.g., gel) blood clotting compositions.

In one embodiment, the blood clotting composition described herein has a prothrombin time that is within normal reference range. As described elsewhere herein, the prothrombin time ("PT") is a measure of the extrinsic pathway of coagulation, and evaluates the coagulation factors VII, X, V, II, and fibrinogen. The time period it takes for clot formation time to occur is the PT. The normal reference range of PT represent an average value of healthy people who live in a particular region, and the range may vary from region to region and over time. The normal reference range may vary depending on the laboratory and test. However, the normal reference range for PT is typically between 9.0-14.0 seconds. The normal range for PT may also be given as a number that represents a ratio called the international normalized ratio (INR). The normal INR is 0.9-1.1.

In another embodiment, the blood clotting composition described herein has a partial thromboplastin time that is within normal reference range. As described elsewhere herein, the partial thromboplastin time ("PTT") or activated partial thromboplastin time ("APTT") is a measure of the intrinsic pathway of coagulation, and evaluates the coagulation factors XII, XI, IX, VIII, X, V, II (prothrombin), and fibrinogen as well as prekallikrein ("PK") and high molecular weight kininogen ("HK"). The time period it takes for clot formation to occur is the partial thromboplastin time ("PPT"). The normal reference range varies by region and by laboratory conducting the test. However, the typical reference range for PPT is 25-50 seconds.

The efficacy of blood coagulation, platelet function, clot strength, and fibrinolysis of the blood clotting composition described herein can also be assessed using thromboelastography ("TEG"). TEG involves adding a sample of whole blood to a rotating cuvette where the low-shear environment mimics a sluggish flow. A plastic pin attached to a torsion wire is lowered into the cuvette. As the blood clots, fibrin strands form between the cuvette and the pin and the torsion of the wire changes. The speed and strength of clot formation are calculated from the change in torsion of the wire, resulting in a cigar-shaped graph. Gross abnormalities of hemostasis can be quickly assessed from the shape of the thromboelastogram. The TEG graph is analyzed for the reaction time ("R-time"), which represents the rate of initial fibrin formation; the speed of clot formation (K-time), which is the time from the end of R until the clot reaches 20 millimeters; the α-angle, which is the tangent of the curve made as the K is reached; and for the maximal amplitude ("MA"), which correlates with the absolute strength of the clot. The α-angle is a measure of the rate of thrombin generation and fibrin formation. A mathematical formula determined by the manufacturer can be used to determine a Coagulation Index (CI) (or overall assessment of coagulability) which takes into account the relative contribution of each of these 4 values into 1 equation. The normal reference ranges for the TEG values are as follows: 5-10 minutes for the R-time; 1-3 minutes for the K-time; 53-72° for the α-angle; 50-70 mm for the MA; and −3 to 3 for the CI. In one embodiment, the blood clotting composition described herein has a TEG values within normal reference range.

In one embodiment, the blood clotting composition described herein has a blood clot initiation time (R-time) of less than three minutes when measured using thromboelastography. In another embodiment, the blood clotting composition described herein has a blot clot initiation time of less than two minutes when measured using thromboelastography. In another embodiment, the R-time of the blood clotting composition is less than 150 seconds, less than 140 seconds, less than 130 seconds, less than 120 seconds, less than 110 seconds, less than 105 seconds, less than 100 seconds, less than 90 seconds, less than 80 seconds, less than 70 seconds, or less than 60 seconds.

Figure 1:
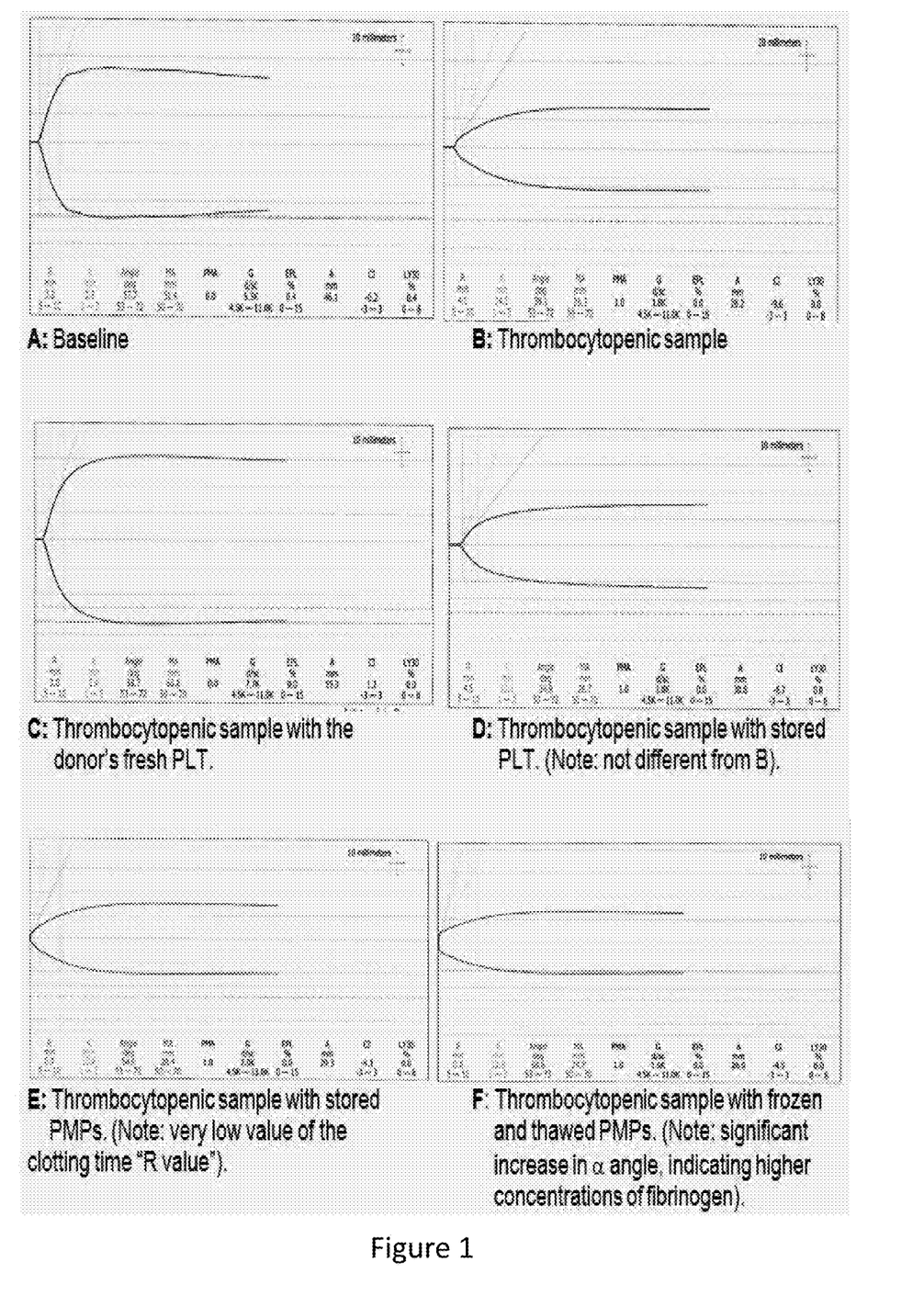
FIG. 1A shows a TEG trace of a normal platelet donor sample at baseline.
FIG. 1B is a TEG trace of a thrombocytopenic sample.
FIGS. 1D-1F are representative TEG traces of thrombocytopenic samples treated (at a ratio of 8:2) with stored platelets (FIG. 1D), stored platelet microparticles (FIG. 1E), or freeze-thawed platelet microparticles (FIG. 1F). The TEG trace shown in FIG. 1F shows a significant increase in the α-angle, indicating higher concentrations of fibrinogen.

By way of example, FIGS. 1A-1F illustrate TEG graphs of platelet blood samples. In particular, FIG. 1B illustrates a TEG graph of a thrombocytopenic samples, FIG. 1C shows a TEG graph of a thrombocytopenic sample with the donor's fresh platelets, and FIG. 1E shows a TEG graph of a thrombocytopenic sample treated with stored PMPs. Note that very low R-time in FIG. 1E compared to the R-time of FIG. 1C. These graphs illustrate the difference clotting time between thrombocytopenic samples treated with fresh vs stored platelet preparations.

The blood clotting composition may be formulated for topical administration. Exemplary topical formulations include, without limitation sprays, powders, creams, gels, ointments, lotions, plasters, bandages, films, dressings, or bioabsorbable patches that can be applied topically to the area in need of treatment. Alternatively, the blood clotting composition is formulated for systemic administration. For example, the blood clotting compositions may be formulated as a liquid (e.g., solution, dispersion, suspension, or emulsion).

Formulation of the blood clotting compositions described herein will mainly depend on the form of administration chosen. Physiologically acceptable carriers, vehicles, and/or excipients for use with the blood clotting compositions of the present invention can be routinely selected for a particular use by those skilled in the art. These include, but are not limited to, solvents, buffering agents, inert diluents or fillers, suspending agents, dispersing or wetting agents, preservatives, stabilizers, chelating agents, emulsifying agents, anti-foaming agents, ointment bases, penetration enhancers, humectants, emollients, and skin protecting agents.

Examples of solvents include water, Ringer's solution, U.S.P., isotonic sodium chloride solution, alcohols, vegetable, marine and mineral oils, polyethylene glycols, propylene glycols, glycerol, and liquid polyalkylsiloxanes. Inert diluents or fillers may be sucrose, sorbitol, sugar, mannitol, microcrystalline cellulose, starches, calcium carbonate, sodium chloride, lactose, calcium phosphate, calcium sulfate, or sodium phosphate.

Examples of buffering agents include citric acid, acetic acid, lactic acid, hydrogenophosphoric acid, and diethylamine. Suitable suspending agents include, for example, naturally-occurring gums (e.g., acacia, arabic, xanthan, and tragacanth gum), celluloses (e.g., carboxymethyl-, hydroxyethyl-, hydroxypropyl-, and hydroxypropylmethylcellulose), alginates and chitosans. Examples of dispersing or wetting agents are naturally-occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to the blood clotting compositions described herein to prevent microbial contamination that can affect the stability of the formulation and cause infection in the patient. Suitable examples of preservatives include parabens (such as methyl-, ethyl-, propyl-, p-hydroxy-benzoate, butyl-, isobutyl- and isopropyl-paraben), potassium sorbate, sorbic acid, benzoic acid, methyl benzoate, phenoxyethanol, bronopol, bronidox, MDM hydantoin, iodopropylnyl butylcarbamate, benzalconium chloride, cetrimide, and benzylalcohol. Examples of chelating agents include sodium EDTA and citric acid.

Examples of gel bases or viscosity-increasing agents are liquid paraffin, polyethylene, fatty oils, colloidal silica or aluminum, glycerol, propylene glycol, carboxyvinyl polymers, magnesium-aluminum silicates, hydrophilic polymers (such as, for example, starch or cellulose derivatives), water-swellable hydrocolloids, carragenans, hyaluronates, and alginates. Ointment bases suitable for use in the pharmaceutical compositions of the present invention may be hydrophobic or hydrophilic; and specific examples include paraffin, lanolin, liquid polyalkylsiloxanes, cetanol, cetyl palmitate, vegetable oils, sorbitan esters of fatty acids, polyethylene glycols, and condensation products between sorbitan esters of fatty acids, ethylene oxide (e.g., polyoxyethylene sorbitan monooleate), and polysorbates.

In certain embodiments, the blood clotting compositions described herein, may, alternatively or additionally, comprise other types of excipients including, thickening agents, bioadhesive polymers, and permeation enhancing agents.

Thickening agents are generally used to increase viscosity and improve bioadhesive properties of pharmaceutical compositions. Examples of thickening agents include, but are not limited to, celluloses, polyethylene glycol, polyethylene oxide, naturally occurring gums, gelatin, karaya, pectin, alginic acid, and povidone. In certain embodiments, a thickening agent is selected for its thioxotropic properties (i.e., has a viscosity that is decreased by shaking or stirring). The presence of such as an agent in a blood clotting composition allows the viscosity of the composition to be reduced at the time of administration to facilitate its application, e.g., to a skin area to be repaired, and to increase after application so that the composition remains at the site of administration.

Another aspect of the disclosure relates to a wound dressing that comprises a blood clotting composition as described herein and a wound dressing material. The wound dressing material comprises any material applied to a wound for protection, absorbance, drainage, etc. For example, the wound dressing material may comprise gauze films (e.g., polyurethane films), hydrocolloids (hydrophilic colloidal particles bound to polyurethane foam), hydrogels (crosslinked polymers containing about at least 60% water), foams (hydrophilic or hydrophobic), calcium alginates (nonwoven composites of fibers from calcium alginate), cellophane (cellulose with a plasticizer), alginate, polysaccharide paste, granules, and/or beads. Suitable wound dressing materials are known in the art and include, without limitation, those disclosed in U.S. Patent Publication No. 2007/0270730 to Rische, U.S. Patent Publication No. 2004/0243044 to Penegor, U.S. Pat. No. 7,652,190 to Johnson, and U.S. Pat. No. 4,363,319 to Altshuler, which are hereby incorporated by reference in their entirety.

In accordance with this aspect, the wound dressing material can be coated with the blood clotting compositions described herein. Alternatively, the wound dressing material may be impregnated with the blood clotting composition described herein.

The blood clotting composition of the present disclosure and/or wound dressings may also contain other coagulation acceleration agents such polyphosphate, and antibiotics, antifungals, anti-infectives, antimicrobials, anti-inflammatories, analgesics, antihistamines and combinations thereof.

The blood clotting compositions described herein are useful for promoting blood clot formation in a subject. Accordingly, another aspect is directed to a method of promoting blood clot formation in a subject that is bleeding. This method comprises administering a blood clotting composition to the subject in a concentration effective to promote blood clot formation.

In accordance with this aspect, the subject can be any animal, including, but not limited to mammals. For example, the subject may be a human, primate, dog, cat, rodent, bird, cow, sheep, horse, goat, pig, etc. In one embodiment, the subject is a human subject.

In one embodiment, the bleeding in the subject is due to a wound or trauma. In another embodiment, the bleeding in the subject is due to surgery. Administration of the blood clotting composition to the subject enhances or increases the rate of blood clotting in the subject to slow or stop the bleeding. Accordingly, the blood clotting composition is administered in a suitable dosage that is effective to induce or enhance the desired blood clotting. The administration of the blood clotting composition described herein may, in some cases completely stop the bleeding, or in other cases, reduce or inhibit the amount of bleeding thereby acting as an aid in the normal clot forming process. Preferably, the lowest effective dose that can contribute to the desired blood clotting is utilized. The optimal dosage and frequency of application will vary depending on the wound or surgical site and can be determined using techniques readily known to one of skill in the art.

In another embodiment, the subject suffers from a bleeding disorder or disease, such as immune or idiopathic thrombocytopenic purpura, drug- and chemotherapy-induced thrombocytopenia and other thrombocytopenias, von Willebrand disease, hemophilia and other inherited or acquired coagulation disorders. Thrombocytopenias of various causes such as idiopathic thrombocytopenic purpura, therapeutic or accidental exposure to cytotoxic agents causing thrombocytopenia (e.g. cancer chemotherapy), or impaired platelet functions caused by drugs or systemic illness or congenital or acquired forms. In this embodiment, administration of the blood clotting composition to the subject enhances or increases the rate of blood clotting in the subject to slow or stop bleeding whenever necessary, e.g., instances of bleeding brought on by more routine procedures such as dental extraction, smaller wounds, etc. In this embodiment, the blood clotting composition is administered in a suitable dosage that is effective to overcome the bleeding disorder to induce or enhance the desired blood clotting. The optimal dosage and frequency of application will vary depending on the disorder and the source of bleeding, but can be determined using techniques readily known to one of skill in the art.

The blood clotting composition can be administered to a subject by someone else, e.g., a health care practitioner, or can be administered to the subject by the subject, i.e., self-administration. The composition can be administered by direct, topical administration to the site of bleeding or to a site immediately adjacent to the site of bleeding, for example using the wound dressing described herein. Alternatively, the composition can be administered by infusion or injection.

The blood clotting compositions described herein offer several advantages to platelet compositions known in the art and currently available in clinical practice. Of note, adverse reactions due to the large volume of plasma required (about 250 ml per platelet unit) are common following platelet transfusion (reported incidence range from 5 to 31%). The platelet microparticle blood clotting compositions intended for systematic use described herein are free of donor plasma, obviating this adverse reaction. On the other hand, and to benefit from the concentrated coagulation factors present in the product, removing donor plasma is not important in the topical applications since adverse reactions here are anticipated to be very minimum to almost negligible; very limited exposure. Thus, the compositions described herein may significantly reduce the needs for platelet transfusion, improve platelet inventory, and, most importantly, reduce adverse transfusion reactions. Table 1 summarizes the benefits of the blood clotting compositions of the present disclosure in comparison with existing platelet products known in the art (i.e., blood bank platelet units).

TABLE 1

Comparison of PMP Compositions to Blood Bank Platelet Units Known in the Art.

| Criteria | Blood Bank Platelet Units | PMP Composition for Systemic Use | PMP Composition for Topical Use |
|---|---|---|---|
| Manufacturer | Blood collection centers (Medical Technicians/Nurses) | Pharmaceutical Company | Pharmaceutical Company |
| Collection Procedures | Manual; apheresis technique; special citrated gas permeable bags | Apheresis technique; regular citrated anticoagulated bags | Apheresis technique; regular citrated anticoagulated bags |
| Shelf Life | 5 days (2-3 days after exclusion of infectious disease testing) | Anticipated 12 months (could be longer) | Anticipated 12 months (could be longer) |
| Storing Condition | Room temperature; shaker; specific humidity and oxygen requirements | Short-term storage at 4° C.; long-term storage at −20° C. and −80° C.; no specific requirements | Short-term storage at 4° C.; long-term storage at −20° C. and −80° C.; no specific requirements |
| Buffer | Donor plasma | 0.9% normal saline or Phosphate Buffered Saline (PBS) or MP Buffered Solution (MPBS): Sodium Chloride: 5.26 g/L Potassium Chloride: 0.37 g/L Sodium Gluconate: 5.2 g/L Sodium Acetate: 3.68 g/L Magnesium Chloride: 0.30 g/L pH = 7.4 | Donor plasma |
| Transfusion Preparation | Identical ABO is preferred; volume depleted (in volume overload risk patients: newborns, babies, chronic renal failure, congestive heart failure, pulmonary edema, etc.); washing (in patients with history of allergic reaction) | None; all products will be collected from group O male donors, filtered, washed, pathogenic treated, and concentrated. | Same as in the systemic applications except the washing step. |
| Administration Location | Hospital | Hospital | Anywhere |
| Administering Personnel | Nurses; medical doctors; or anesthesia technicians | Nurses; medical doctors; or anesthesia technicians | Anyone (Self, EMS, military personnel, etc.) |
| Risk of Bacterial or Viral Contamination | Very High | Almost none (disinfected for any possible bacterial or viral contamination) | Almost none (disinfected for any possible bacterial or viral contamination) |
| Complications | Allergic reactions (donor's plasma proteins); febrile non-hemolytic (donor's WBC or mediators); hemolysis (donor's ABO antibodies); volume overload (large volumes); TRALI (donors WBC and/or HLA antibodies) | Conceivably none (compositions are filtered, washed, and concentrated) | Allergic reaction is possible; but very negligible due to the topical application. |
| Development of anti-Platelet antibodies | Very likely in transfusion dependent patients (ITP, cancer, etc.) | Possible (only in multi-exposures) but the use of only group O male donors will minimize this effect significantly. | None |
| Thrombotic Risk | Very likely, especially in cancer transfusion dependent patients | Less likely since donor plasma is removed | None |
| Supernatant | Contains several harmful inflammatory mediators accumulated during storage at room temperature (AKA storage lesions) | None; washed product and no room temperature storage | No room temperature storage |

Another aspect is directed to a method of preparing a composition of platelet microparticles having coagulation activity. In general, this method comprises the following steps: obtaining a sample of fresh platelet rich plasma; subjecting said sample to one or more freeze-thaw cycles; sonicating the subjected sample to induce platelet microparticles production in the sample; separating a platelet microparticle fraction from other components in the sonicated sample; and resuspending the separated platelet microparticles in an isotonic solution.

As described elsewhere herein, the isolated platelet microparticles of the present invention can be obtained from any source. In general, fresh platelet rich plasma can be obtained from fresh donor blood, less than one day old.

Thus, for example, fresh platelet rich plasma can be obtained immediately following collection of donor blood. Preferably, platelet rich plasma is obtained less than 24, 20, 15, 10, 5, 2, 1, 0.5, or 0.25 hours following collection of donor blood.

The platelet rich plasma can be subject to one or more freeze-thaw cycles. In one embodiment, the platelet rich plasma is subject to one freeze-thaw cycle. In general, the platelet rich plasma is incubated at a temperature below freezing for at least a sufficient time for the sample to freeze. The sample is then incubated at a higher temperature for at least a sufficient time for the sample to thaw. As used herein, the term "freeze-thaw cycle" is intended to refer to the process by which a sample is first frozen by cooling and then thawed by heating. For example, freshly collected platelet rich plasma is frozen at −20° C. for at least one hour to at least overnight or longer. Alternatively, the freshly collected platelet rich plasma is frozen at −80° C. for at least one hour to at least overnight or longer. Once frozen, the sample can be thawed at 37° C. for less than one hour, less than 45 minutes, less than 30 minutes, less than 15 minutes, less than 10 minutes, or less than 5 minutes.

In one embodiment, the separated microparticle fraction comprises, in addition to the platelet microparticles, effective amounts of one or more coagulation factors. Exemplary coagulation factors are described supra and include, without limitation fibrinogen, von Willebrand factor, Factor V, Factor VII, Factor VIII, and Factor XI.

According to this aspect, the method of preparing a composition of microparticles comprises sonicating the freeze-thawed platelet rich plasma sample to induce platelet microparticle production. As used herein, "sonicating" refers to applying high frequency sound energy (to agitate particles) such as, but not limited to, ultrasound. Such exposure can be performed by employing sound frequencies of, for example, and without limitation, about 10 kHz to about 1,000 kHz. For sonication, a variety of commercially available instruments, well known to the skilled artisan, may be utilized as a source of the sound waves used in the present methods. Sonication may be carried out continuously or in multiple cycles, where each cycle includes an "on" state of certain duration and an "off" state of certain duration. In a preferred embodiment of the present invention, the method of preparing a composition of microparticles comprises pulsed sonication.

This method of preparing a composition of microparticles further comprises separating a platelet microparticle fraction from other components in the sonicated sample. For example, platelet microparticles may be separated from other components in the sonicated sample by any suitable method, including, but not limited to, filtration, centrifugation, or ultracentrifugation. In one embodiment, the method of preparing a composition of microparticles comprises ultracentrifuging the sample for greater than 10 minutes, greater than 20 minutes, greater than 30 minutes, greater than 40 minutes, greater than 50 minutes, or greater than 60 minutes to generate a platelet microparticle pellet.

The separated platelet microparticles are resuspended in an isotonic solution. As is known in the art, solutions suitable for resuspension of platelets include several salt solutions, including, but not limited to, solutions comprising sodium chloride (NaCl) and potassium chloride (KCl), e.g., PBS.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Generation of Platelet Microparticles from Stored Blood

To generate a concentrated PMP composition, platelets were isolated using a novel technique utilizing freshly collected platelets. Following blood collection from normal donors, platelet rich plasma samples were processed and frozen immediately at −20° C. overnight. Frozen samples were then thawed at 37° C. for 5 minutes. Platelet microparticles were separated from other components in the serum sample and resuspended in an isotonic solution.

Example 2: Thromboelastography Analysis of PMPs from Stored Blood

To evaluate the ability of non-sonicated platelet microparticle ("PMP") compositions to mediate coagulation activity, a protocol known in the art was used to prepare fresh platelet ("PLT") and stored platelet compositions. Five donor samples of PMPs, fresh PLTs, and stored PLTs were evaluated using thromboelastography ("TEG"). Of note, all experiments were performed on samples of normal PLT count (250-300×$10^9$/L).

Samples were tested at baseline, at thrombocytopenic status, and after treating the thrombocytopenic samples with fresh PLTs, stored PLTs, and PMPs at a ratio of 8:2. FIG. 1A-E shows that PMPs generated from stored PLTs have significantly greater beneficiary effects on clot kinetics than stored PLT themselves. Although clot strength (indicated by the maximum amplitude ("MA") parameter of the TEG) was not different between the stored PLT (washed or non-washed) and PMPs, PMPs significantly reduced the clot initiation time (shorter R-time), and increased the rate of thrombin generation and fibrin formation (increased a angle) (Table 2). The coagulation index ("CI") is an overall assessment of coagulability of a sample. These findings suggest that PMPs, which mainly contain PLT membranes, are essential in PLT transfusion and are perhaps more important in controlling bleeding than the stored PLTs themselves.

TABLE 2

Thromboelastography Analysis of Platelet and PMP Compositions.

| Sample | R Time | K Time | α angle | Maximum Amplitude (MA) | Coagulation Index (CI) |
|---|---|---|---|---|---|
| Baseline | 3.9 ± 0.8 | 2 ± 1.3 | 57 ± 3 | 60 ± 8 | 0.37 ± 1.2 |
| Thrombocytopenic | 4 ± 0.2 | 6 ± 2.5 | 44 ± 7 | 26 ± 2 | −8.6 ± 1.5 |
| Fresh PLTs | 3.5 ± 0.6 | 2.6 ± 1.1 | 58 ± 1 | 58 ± 5 | 0.4 ± 1.2 |
| Stored PLTs | 4.0 ± 1.1 | 6 ± 1.1 | 40 ± 4 | 36 ± 7 | −5.6 ± 2.3 |
| Fresh PMP after freeze/thaw cycle and ultrasonication | 1.1 ± 0.8* | 2.2 ± 0.9** | 49 ± 4** | 27 ± 13 | −4.4 ± 2.5 |

*p = 0.006;
**p < 0.001 by the t-Student test and in comparison to stored PLTs.

Example 3: Generation of Sonicated Platelet Microparticles from Fresh Blood

Platelet rich plasma ("PRP") was prepared from fresh donor blood, less than one day old. PRP was centrifuged at 250×g for 12 minutes. Next, prostaglandin 12 was added (1 µl/ml PRP) to the sample. The sample was centrifuged for an additional 10 minutes at 800×g. Greater than half the volume of platelet poor plasma ("PPP") was removed from the top. Platelets were resuspended in remaining PPP to concentrate ($1000 \times 10^3$). Samples were then frozen at −80° C. overnight, thawed at 37° C. for 5 minutes, placed on ice, and sonicated (four seconds on/off, 3×) to induce platelet microparticle production. Platelet microparticles were separated from other components in the serum sample by centrifugation at 2,100×g for 12 minutes followed by centrifugation at 18,000×g for 60 minutes. The supernatant was then removed and PMPs were resuspended in ½ the volume Cation-Free Tyrodes Buffer. PMPs were stored on ice until use.

In some instances, the PMP composition is generated as follows:
- Fresh PRP from normal donor (PC, or apheresis)
- Concentrate to specific PLT count (centrifugation)
- Concentrated PLT can be washed at this step (if needed) using stabilizer/diluent
- Freeze immediately at −20° C. for at least 24 hrs
- Thaw at 37° C. water bath for 5-10 min
- UltraSonication at 50 Watts (3 mm probe diameter) for 2 sec on, 2 sec off ×4 (VibraCell Probe Sonicator, Model VC50, Sonics and Materials Inc., Danbury, Conn.)
- Concentrate the final solution by ultrafiltration, ultracentrifugation, or lyopholization

TABLE 3

Components of the final product

| Components | Value Range (Unit) |
|---|---|
| PMP Concentration by NanoSight | $3.9-5.5 \times 10^8$ Particles/mL |
| PMP Concentration by FlowCytometry | $4-5 \times 10^7$/mL |
| PMP size* | 276 ± 14.3 nm |
| pH | 8.2 |
| PLT count | $1 \times 10^{6-7}$/microL |
| WBC | $0-0.2 \times 10^3$/microL |
| Hgb | 0 mg/dL |
| Hct | 0% |
| Fib | 180-368 mg/dL |
| FV | 0.81-0.94 IU |
| FVII | 1.57-2.08 IU |
| FVIII | 0.65-0.78 IU |
| FIX | 0.82-1.45 IU |
| FXI | 1.02-1.49 IU |
| FXII | 1.95-4.53 IU |
| vW Ag | 146-191% |
| vW Act | 23-40% |
| PC | 105-142% |
| PS | 54-62% |
| ATIII | 85-105% |

Example 4: Thromboelastography Analysis of Sonicated PMPs from Fresh Blood

Platelet microparticle formulations comprising sonicated PMPs isolated from fresh blood were compared against Fresh PLTs. Briefly, six PLT donor samples were evaluated by TEG. Samples were tested at baseline, at thrombocytopenic status, and after treating the thrombocytopenic samples with fresh PLTs and PMPs of thawed, ultra-sonicated fresh PLT at a ratio of 8:2. Data are shown as a mean±SEM. Table 2 shows that the efficacy of the PMP composition was further improved by the processing of platelet rich plasma from fresh blood and the addition of a sonication step. All experiments were performed in samples of normal platelet count ($250-300 \times 10^9$/L).

Example 5: Efficacy of Inventive Platelet Micro Particle Composition Compared to Prior Art Composition To test the efficacy of the PMP compositions described herein, the inventive compositions were compared to PMP compositions known in the art. The prior art compositions and methods of making the same are described in detail in WO 1990012581 A1 to Chao ("Chao"), 2006/0034809 A1 to Ho et al. ("Ho"), and U.S. Pat. No. 8,105,632 to Jy et al. ("Jy"), which are hereby incorporated by reference in their entirety.

Chao describes the generation of platelet microparticles from stored blood. To produce the PMP composition of Chao, stored platelet concentrates were pooled in blood bags and centrifuged at 1,000 rpm for 11 minutes at 22° C. to remove contaminating red and white blood cells. The supernatants, which contained the platelets, then were transferred to new blood bags and centrifuged at 3,000 rpm for 25 minutes at 22° C. to separate platelets from plasma. Platelet-poor plasma was expressed and each of the resulting platelet pellets was gently resuspended in 100 mL of a 0.9% NaCl solution (physiological saline) and pelleted by centrifugation at 3,000 rpm for 20 minutes at 22° C. The supernatant was removed and the platelet pellet was washed twice with physiological saline by repeated resuspension and centrifugation. Washed platelets were finally resuspended in physiological saline and disrupted by repeated freezing (at −80° C. for at least six hours) and thawing (at 25° C. for at least one hour), three times. The frozen and thawed suspension was diluted with physiological saline and centrifuged at 3,000 rpm for 30 minutes to collect a platelet ghost pellet. This platelet ghost pellet was resuspended in physiological saline and washed twice by repeated resuspension and centrifugation. The washed ghost pellet was resuspended in physiological saline and heated to 100° C. for five minutes. A gross precipitate developed during the heat treatment. This heat-treated, platelet ghost suspension was homogenized with a sonicator by pulsing at 20 kHz for 5 minutes and 48 seconds (2 second cycle, 1.4 seconds on, 0.6 seconds off). The sonicated preparation next was centrifuged at 3,000 rpm for 30 minutes at RT to separate the precipitated material from the formed platelet membrane microparticles which remain in the supernatant. The supernatant was removed and stored in sealed containers at 4° C.

U.S. Pat. App. Publ. 2006/0034809 A1 describes the generation of a freeze-dried preparation containing stabilized platelets and platelet microparticles as tissue regenerative and non-infusible hemostat. To generate the PMP composition of Chao, platelet rich plasma (PRP) was obtained by low speed centrifugation (135×g for 15 minutes) of platelets. The centrifuged PRP (without red blood cells) was acidified to pH 6.6-6.8 by adding acid citrate dextrose and then pelleted by centrifuge at 1500×g for 15 minutes. The platelet-poor plasma was decanted, residual liquid containing plasma proteins was removed, and the packed cells were resuspended in 1 ml of Cation-Free Tyrodes Buffer containing 50 mM of trehalose at pH 6.8. The platelet concentration was adjusted to $1.25 \times 10^9$/ml. The mixture was then incubated for 2 hours at 37° C., mixing once each half hour.

Jy describes three alternative methods for PMP production, each of which was prepared for this Comparative Example as described elsewhere herein.

The first method of Jy relates to the preparation of platelet microparticles from stored blood. To generate this composition of Jy, platelets expired by 1-5 days were sedimented by centrifugation 10 min at 200×g, room temperature. The supernatant was removed and diluted to double volume by adding PBS/citrate, then the microparticles were sedimented by centrifuging 8,000×g for 30 min. PMPs are resuspended in saline and refrigerated for storage.

The second method described by Jy relates to the preparation of PMPs using the ultrasonic method. To generate this composition of Jy, fresh or recently expired platelets were washed twice in PBS buffer with 1 mM EDTA/5 mM MgSO$_4$, and were sonicated in a 50 mL polypropylene tube for 3-5 bursts of 3-5 seconds each at room temperature. Residual platelets and debris were removed by centrifugation for 10 min at 200×g, and the PMP in the supernatant were sedimented by centrifugation at 8,000×g for 30 minutes. The pellet was washed with PBS with 1 mM EDTA/5 mM MgSO$_4$.

The third method described by Jy relates to the preparation of PMPs using the calcium activation method. To generate this composition of Jy, 1.0 mL of washed platelets were suspended at $2.5 \times 10^5$/uL in HEPES/saline pH 7.4. Platelets were activated with thrombin/collagen combination and gently agitated for twenty minutes at room temperature. Samples were centrifuged at 200×g for 10 min, and PMP were recovered from supernatant by centrifugation at 8,000×g for 30 minutes, resuspension in a PBS/citrate solution, and washed prior to use.

Figure 2A:
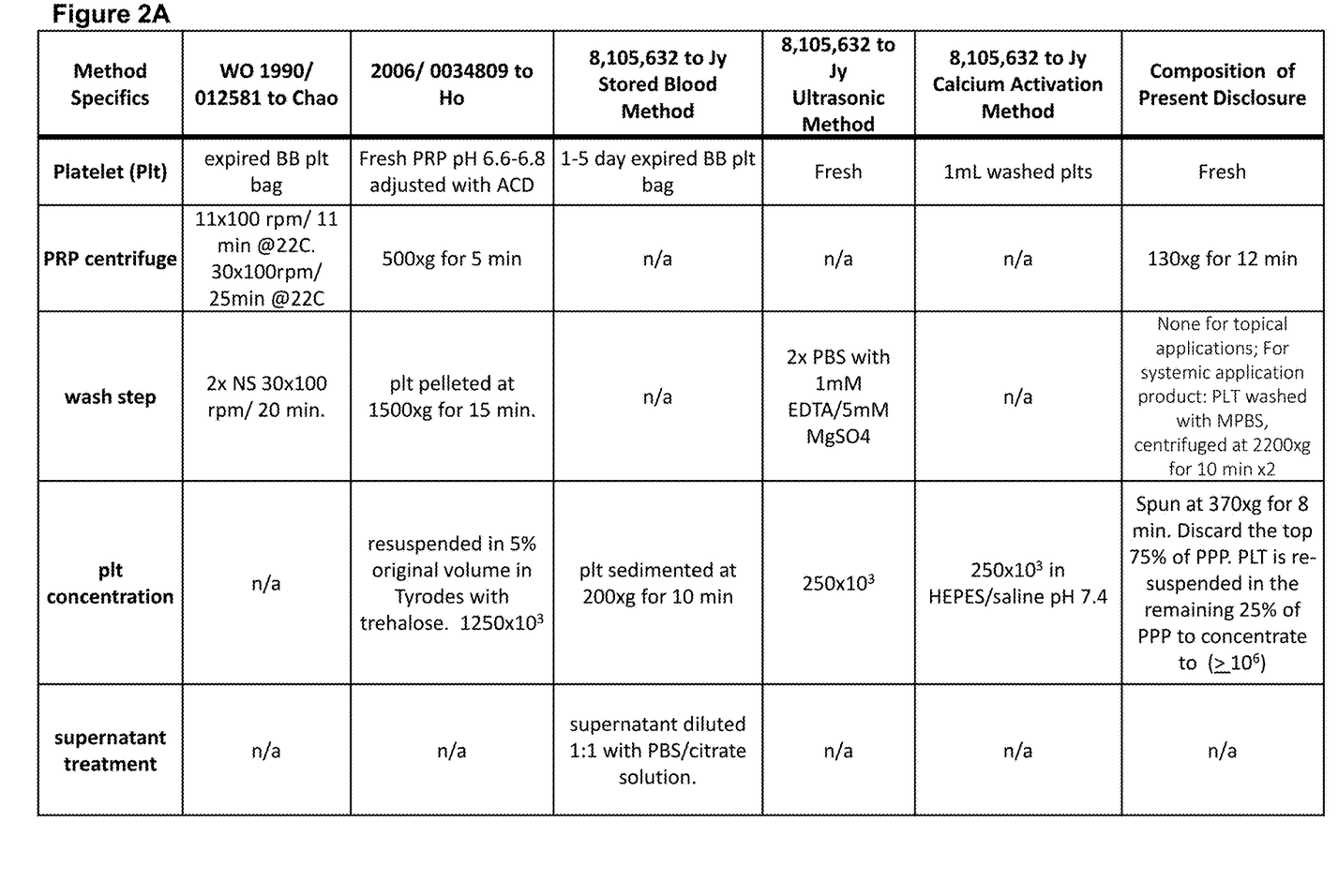
FIGS. 2A-2C are images demonstrating the comparison of methods for PMP isolation.
Figure 2B:
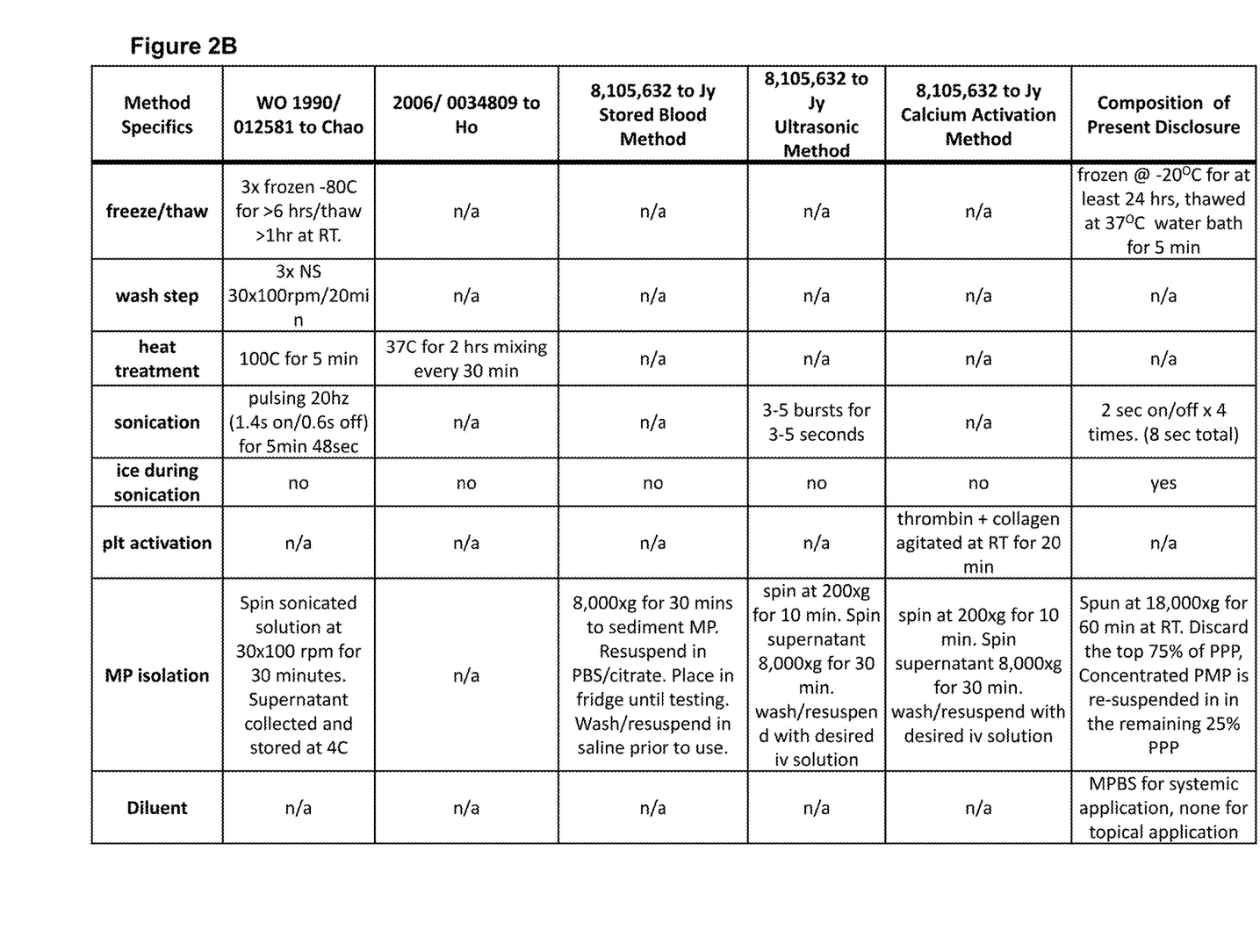
Figure 2C:
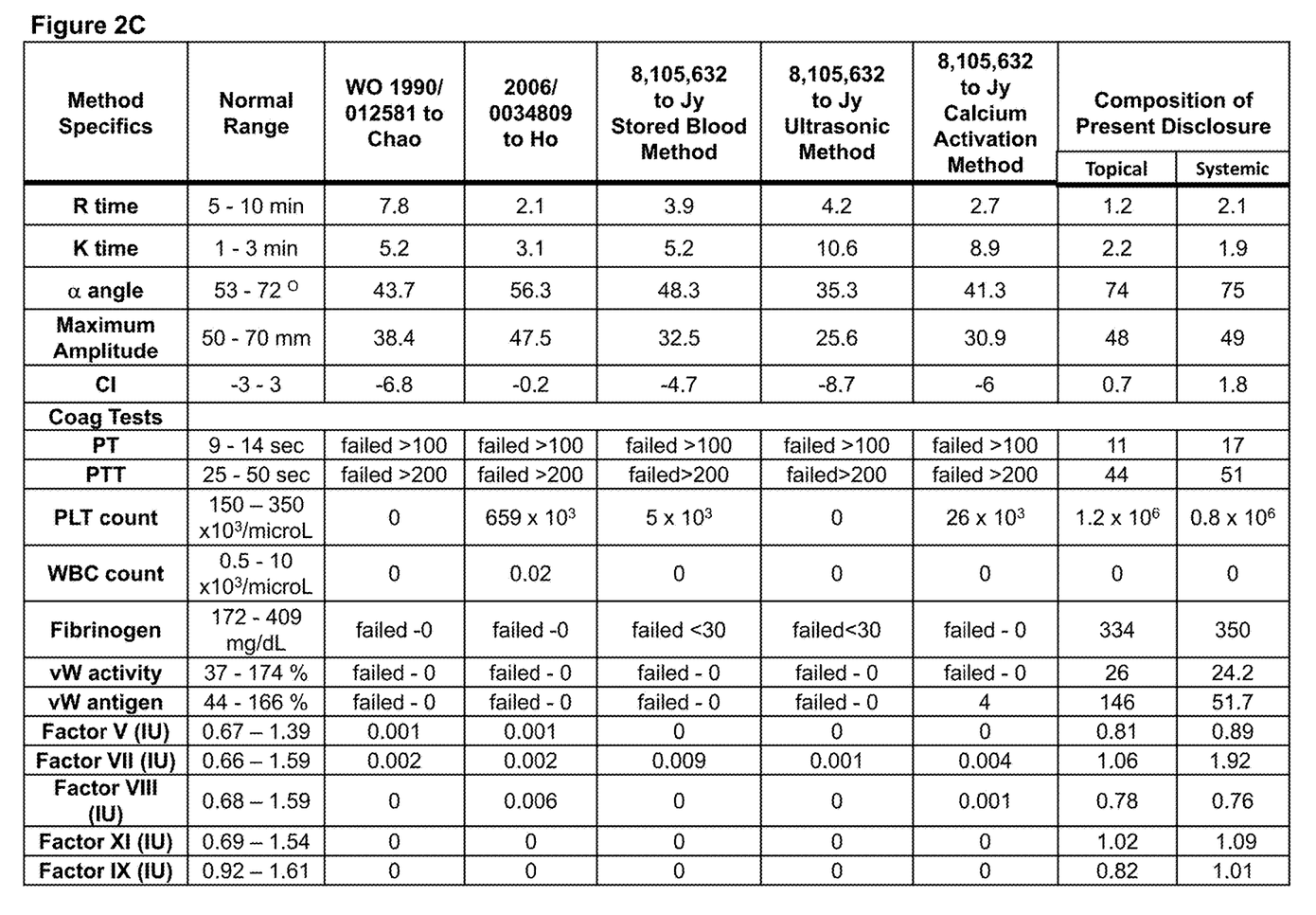
Figure 3:
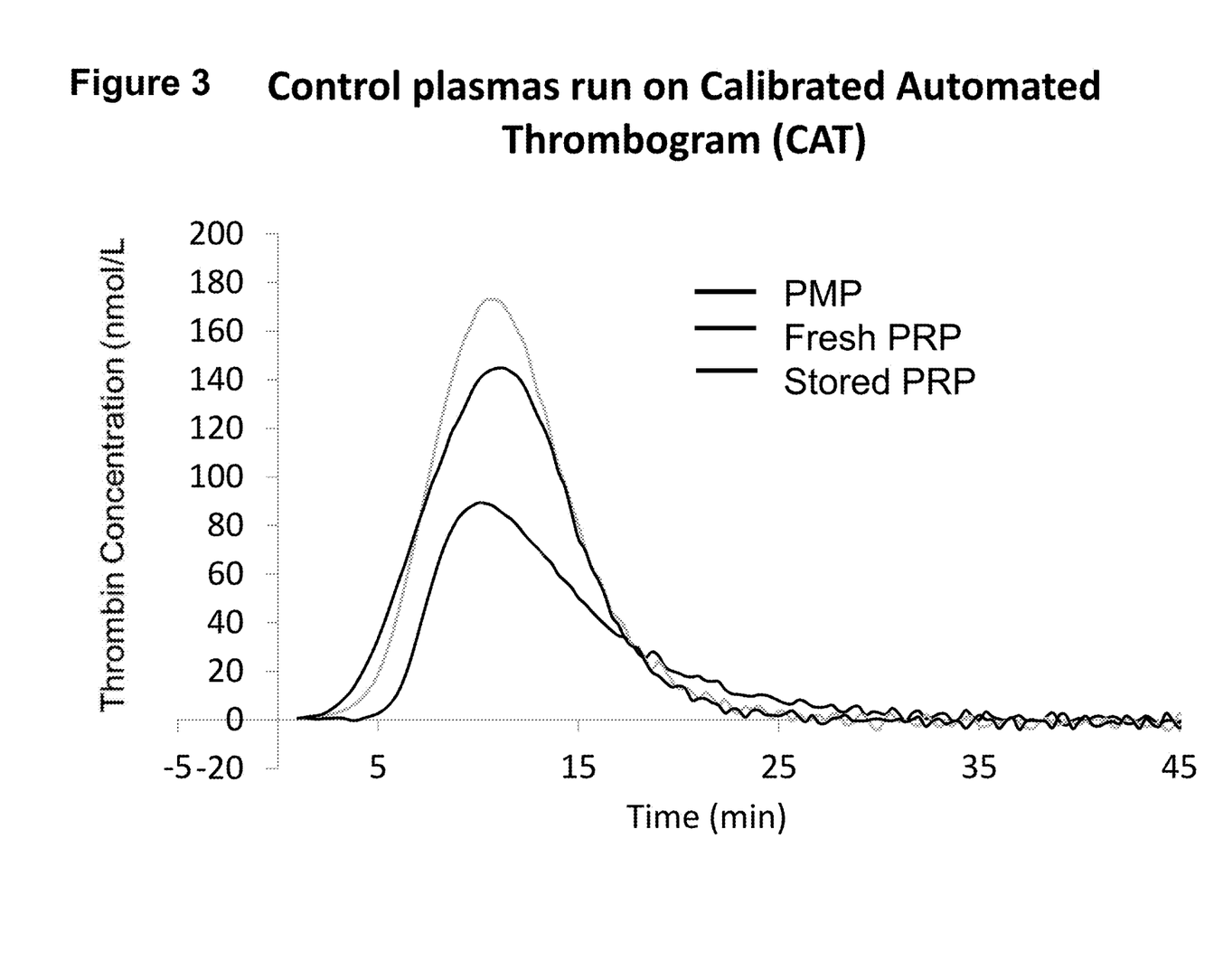
FIG. 3 is an image summarizing thrombin generation assay data.
Figure 4:
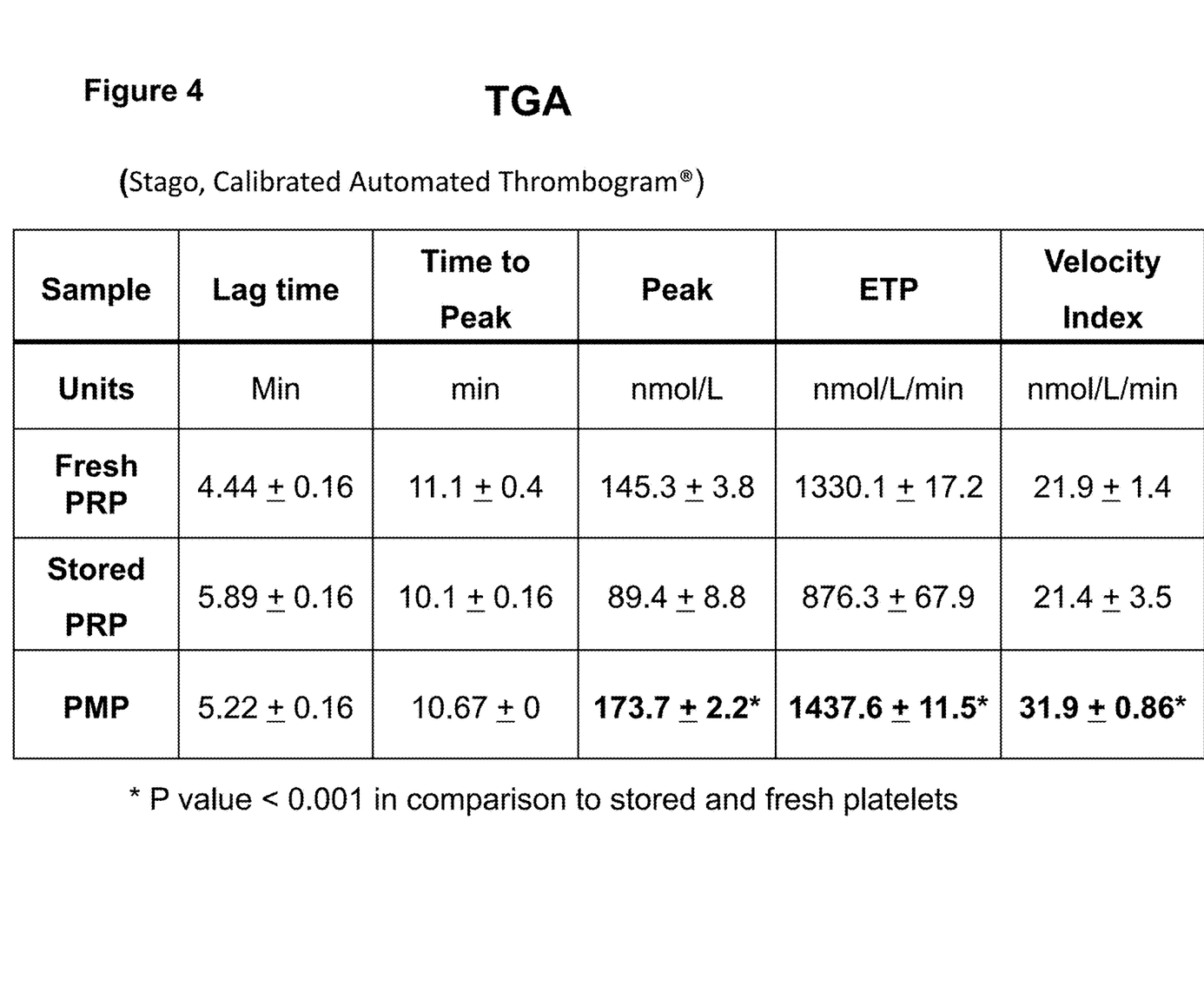
FIG. 4 is an image showing TGA results.

FIG. 2 compares the method of preparing the PMP composition described herein (Example 3) to the methods of Chao, Ho, and Jy.

As described elsewhere herein, patient hemostasis is often evaluated by analyzing a patient blood sample for platelet counts, various markers involved in blood clotting, and clot forming ability, including the amount of time it takes to clot initiation. The coagulation assays measuring the prothrombin time ("PT") and the partial thromboplastin time ("PTT") are used to evaluate the extrinsic and intrinsic coagulation pathways, respectively. Thromboelastography ("TEG") measures platelet function, clot strength, and fibrinolysis by triggering clot formation followed by computerized coagulation analysis.

The blood clotting composition described herein was compared to prior art blood clotting compositions to demonstrate the improved efficacy of the composition disclosed herein. In particular blood coagulation was assessed by TEG analysis and the results for all compositions are summarized in FIG. 2C elsewhere herein. The prothrombin time (PT) and partial thromboplastin time (PTT), two other measures of clotting time were also analyzed and compared. Finally, the presence and activity of several coagulation factors was also measured in the various compositions.

As shown in FIG. 2C, the platelet microparticle blood clotting composition described herein is the only composition to present PT, PTT, and TEG values within the normal range. The normal range of values expected for the various coagulation assays and TEG is also provided in FIG. 2C. Importantly, the composition of the present disclosure was the only composition comprising normal ranges of fibrinogen, vW antigen, Factor V, Factor VII, Factor VIII, and Factor XI activity. Accordingly, the blood clotting composition of the present disclosure is clearly a distinguishable improvement to prior art compositions.

Example 6: Development of a Concentrated Platelet Microparticle Blood Clotting Composition for Topical Administration To test the hypothesis that improved hemostasis in bleeding patients following platelet transfusion is related to the concentration of platelet microparticles generated during platelet collection, preparation, and storage; a concentrated PMP product will be prepared. The concentrated PMP product will be developed for topical administration and will contain washed fresh human PMPs suspended in 0.9% saline in a format that allows long-term storage (up to 12 months).

A thrombocytopenic mouse model will be used to assess the efficacy of the PMP blood clotting composition of the present invention in vivo. A potent platelet inhibitor will be administered to these animals to eradicate any possible internal platelet function. Testing will be performed in both control animals (6 animals each), and a combination of 2 different injury locations (chest or abdomen and thigh), 2 depths (shallow and moderate; to include muscles), and 3 lengths (½, 1, and 2 cm). Following the induction of local skin injury, the PMP composition of the present invention will be applied (soaked bandages) locally with minimum pressure. Differences in the amount and duration of bleeding between study and control animals will be assessed by an animal expert laboratory research assistant blinded to the treatment. Normal saline soaked bandages will be used in control animals. Injury characteristics (length, depth, and location) and the time duration of application of the anticipated product will be regulated between all animals.

Example 7: Development of a Concentrated Platelet Microparticle Blood Clotting Composition for Systemic Administration The concentrated PMP product will also be developed for systemic administration. This composition will be tested in the thrombocytopenic mouse model described elsewhere herein. Two different groups of animals will go under identical small bowel surgery. The proposed product will be applied topically on the operational sites. Bleeding amount and duration of the small bowel will be assessed between the study and the control groups (normal saline soaked bandages will be used in the control arm).

The next set of experiments will include IV injections of different concentrations of the proposed PMP product into a bleeding animal. Clinical outcomes will be compared between the study animals and the control animals who will receive IV infusions of the stored PLT products (only in this set of experiments).

Example 8: Evaluation of Long-Term Storage Potential of the PMP Composition of the Present Invention The concentrated PMP product will be evaluated for the ability to maintain hemostatic effectiveness over prolonged periods of time following storage at 20° C.

Example 9: Thrombocytopenic Model

Experiments were designed to develop a severe thrombocytopenic bleeding model. The PMP product can be administered to the thrombocytopenic model at 2:8 ratio. Experiments can be performed to evaluate changes from baseline and thrombocytopenic model utilizing various assays such as Thromboelastography (TEG), Activated Clotting Time (ACT), Thrombin Generation Assay (TGA), Whole blood Aggregation (WB-Agg), and the likes.

Experiments can also be performed to measure PMP size and concentrations by NanoSight. Identify of PMP and measurement of PMP activity can be assessed by Flowcytometry.

What is claimed:

1. A blood clotting composition comprising:
   isolated platelet microparticles obtained from fresh blood, wherein the concentration of platelet microparticles in the composition is $>10^7$ microparticles/µl; fibrinogen (Factor I), von Willebrand factor, Factor II, Factor V, Factor VII, Factor VIII, Factor IX, Factor X, Factor XI, Factor XII, Protein C (PC), Protein S (PS), antithrombin III (ATIII); and a pharmaceutical carrier; wherein fibrinogen is at about 100-400 mg/deciliter (dL), Factor V is at about 0.5-1.00 International Unit (IU)/ml, Factor VII is at about 1.0-2.5 IU/ml, Factor VIII is at about 0.5-1.00 IU/ml, Factor IX is at about 0.5-1.50 IU/ml, Factor XI is about 0.5-2.00 IU/ml, Factor XII is at about 1.5-5.00 IU/ml, Protein C (PC) is at about 100-200% activity as compared to a normal plasma pool having 100% activity, Protein S (PS) is at about 10-70% activity as compared to a normal plasma pool having 100% activity, antithrombin III (ATIII) is about 25-110% activity as compared to a normal plasma pool having 100% activity.

2. The composition of claim 1, wherein the composition has either prothrombin time that is within a normal reference range or an activated partial thromboplastin time that is within a normal reference range.

3. The composition of claim 1, wherein the composition has a blood clot initiation time (R-time) of less than three minutes when measured using thromboelastography.

4. The composition of claim 1, wherein the concentration of platelet microparticles in the composition is $>10^{14}$ microparticles/µl.

5. The composition of claim 1, wherein the composition is formulated for topical administration or systemic administration.

6. The composition of claim 5, wherein the composition is formulated as a spray, powder, cream, gel, or ointment.

7. A wound dressing comprising:
   the blood clotting composition of claim 1 and
   a wound dressing material.

8. The wound dressing of claim 7, wherein the wound dressing material comprises gauze.

9. The blood clotting composition of claim 1, wherein the composition is made by a method comprising:
   obtaining a sample of fresh platelet rich plasma;
   subjecting said sample to one or more freeze-thaw cycles;
   sonicating the subjected sample to induce platelet microparticle production in the sample;
   separating a platelet microparticle fraction from other components in the sonicated sample; and
   resuspending the separated platelet microparticles in an isotonic solution.

10. A method of promoting clot formation in a subject that is bleeding, said method comprising:
    administering the composition of claim 1 to the subject in a concentration effective to promote blood clot formation.

11. The method of claim 10, wherein the bleeding in the subject is due to at least one selected from the group consisting of a wound, trauma, and surgery.

12. The method of claim 10, wherein said composition is administered topically to a site of bleeding.

* * * * *